US007489401B2

(12) United States Patent
Kamei et al.

(10) Patent No.: US 7,489,401 B2
(45) Date of Patent: Feb. 10, 2009

(54) DEVICE FOR DETECTING EMISSION LIGHT OF MICRO-OBJECT

(75) Inventors: Toshihiro Kamei, Tsukuba (JP); Taro Itatani, Tsukuba (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 285 days.

(21) Appl. No.: 11/066,261

(22) Filed: Feb. 28, 2005

(65) Prior Publication Data

US 2005/0237524 A1    Oct. 27, 2005

(30) Foreign Application Priority Data

Mar. 1, 2004    (JP) .............................. 2004-056914

(51) Int. Cl.
   *G01N 21/25* (2006.01)
(52) U.S. Cl. .................................... 356/417
(58) Field of Classification Search ......... 356/317–318, 356/417; 250/458.1–461.2; 422/82.07–82.08; 436/172
   See application file for complete search history.

(56) References Cited

U.S. PATENT DOCUMENTS 6,201,989 B1 *    3/2001 Whitehead et al. .......... 600/476

2003/0222223 A1 *    12/2003 Kamei et al. .............. 250/458.1
2004/0066805 A1 *    4/2004 Afzal et al. ................... 372/10
2005/0046848 A1 *    3/2005 Cromwell et al. ........... 356/417

FOREIGN PATENT DOCUMENTS

WO    WO 03/102554 A1    12/2003

OTHER PUBLICATIONS

Toshihiro Kamei, et al, "Integrated Hydrogenated Amorphous Si Photodiode Detector for Microfluidic Bioanalytical Devices", Analytical Chemistry, vol. 75, No. 20, Oct. 15, 2003, pp. 5300-5305.
Evan Thrush, et al., "Integrated bio-fluorescence sensor", Journal of Chromatography A, vol. 1013, Sep. 26, 2003, pp. 103-110.
Xiaoxi Chen, et al., "A Prototype Two-Dimensional Capillary Electrophoresis System Fabricated in Poly(dimethylsiloxane)", Analytical Chemistry, vol. 74, No. 8, Apr. 15, 2002, pp. 1772-1778.

* cited by examiner

*Primary Examiner*—Tarifur R Chowdhury
*Assistant Examiner*—Jonathon D Cook
(74) *Attorney, Agent, or Firm*—Oblon, Spivak, McClelland, Maier & Neustadt, P.C.

(57) ABSTRACT

In the detection of fluorescence Lf emitted by a micro-object irradiated with an excitation light Le by a semiconductor light-detecting element 20, a converging microlens 62 for converging the excitation light Le elevating the optical density thereof and irradiating the micro-object with the light, causing the micro-object to generate fluorescence Lf due to two-photon absorption, is inserted partway along the light path of the excitation light Le. This enables the fluorescence Lf emitted by the micro-object to be detected with high sensitivity.

15 Claims, 9 Drawing Sheets

F I G. 3
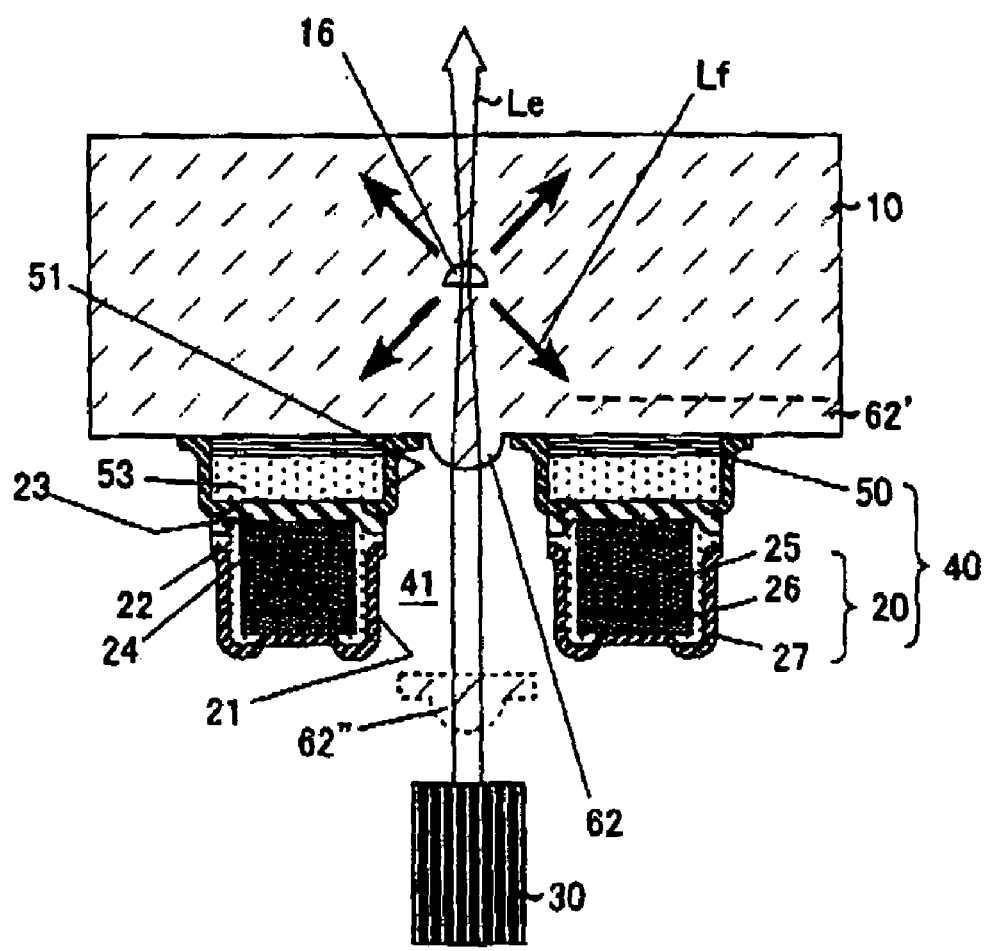

DEVICE FOR DETECTING EMISSION LIGHT OF MICRO-OBJECT

BACKGROUND OF THE INVENTION

Field of the Invention

This invention relates to a device for detecting with high sensitivity emission light emitted in the form of fluorescence or phosphorescence from a micro-object irradiated by an excitation light, and more particularly relates to a device for detecting the emission light of a micro-object which is suitable in cases such as when the micro-object is a fluorophore in biochemical analysis, a semiconductor quantum dot, or a micro-sample labeled with a fluorophore or a semiconductor quantum dot.

The electrophoretic method, for example, constitutes one of the analytic processes which are employed in various biochemical analyses such as, for example, of nucleic acids, amino acids and proteins. Recently, devices have been proposed that are capable of obtaining various sorts of information even from a solution sample of as minute an amount as from a nanoliter to a picoliter by labeling the solution sample with an appropriate fluorophore, irradiating the sample on a compact electrophoretic chip with an excitation light, and subjecting the fluorescence emitted by the fluorophore to analytical processing. With respect to devices of this nature, the present inventors have also provided to date such devices and methods that are disclosed in Document 1: official gazette of International Publication WO 03/102554 and Document 2: T. Kamei et al., "Integrated Hydrogenated Amorphous Si Photodiode Detector for Microfluidic Bioanalytical Devices," Anal. Chem., Vol. 75, No. 20 (Oct. 15, 2003), pp. 5300-5305.

FIG. 10 illustrates one example of a conventional device disclosed by the present inventors in the above Documents 1 and 2.

The following description is based on this diagram. This device has a chip 10 for holding and supporting an analytical sample and this chip 10 is furnished with mutually planar intersecting microchannels 15, 16.

One of these, channel 15 called inlet channel 15, is provided at one end thereof with a well-shaped sample reservoir 11 for containing a sample in the form of a solution and at the other end thereof with a waste reservoir 12 for receiving the sample flowing out via the injection channel 15. The other channel 16 which intersects the injection channel 15, called a separation channel 16, is provided at one end thereof with a cathode reservoir 13 and at the other end thereof with an anode reservoir 14. The reservoirs 11~14 are each provided with electrodes, not shown, in the form of a thin film, or inserted electrodes that are needle-shaped or the like, for the purpose of applying individually preset voltages at the timings described below. The channels 15 and 16 generally intersect each other orthogonally, as illustrated, and, in a planar view, these channels 15 and 16 form the shape of a cross.

When a sample is injected into the sample reservoir 11 and an appropriate voltage is then applied between the sample reservoir 11 and the waste reservoir 12, the sample migrates into the injection channel 15. At this time, the cathode reservoir 13 and the anode reservoir 14 are kept in a floating potential state or an appropriate bias voltage is applied therebetween. When the voltage is switched after the lapse of an appropriate time (generally in the order of 10~60 seconds) and an appropriate voltage is applied between the cathode reservoir 13 and the anode reservoir 14, a part of the sample (called a sample plug) which has just reached the point of intersection with the separation channel 16 is cut out, and electrophoresis begins inside the separation channel 16. Further, at this time, an appropriate bias voltage is applied between the sample reservoir 11 and the waste reservoir 12 so that the residual sample in the injection channel 15 does not flow into the separation channel 16.

By utilizing recent semiconductor microfabrication technology, it is possible to pattern the channels 15 and 16 accurately in a very small width and form a short sample plug corresponding to the channel width (generally some tens of μm). In practice, the chip 10 is usually manufactured often than not by bonding two glass sheets since it is required to possess the highest possible optical transmittance in the wavelength of at least the excitation light or fluorescence and to possess good insulating property to the electrophoresis. That is, the channels 15 and 16 are lithographically (in some cases, mechanically) formed on one glass sheet 10a and subsequently thermal welding is used to affix the other glass sheet 10b which occludes the channels 15 and 16 from above and is perforated with vertical holes to form the reservoirs 11~14. It is also possible to use plastic substrates. The two plate members are bonded by thermal bonding, ultrasonic welding, or the use of an adhesive agent. To state in advance, this invention does not impose any particular restriction on the structure of this part. The structure is only required to have a structure suitable for analysis, and a conventional configuration may be used.

Thus, even with existing fabrication technology, an extremely short sample plug can be obtained and electrophoretic separation with high number of theoretical plates can be achieved in a short channel. The sample migrating inside the separation channel 16 is labeled in advance with an appropriate fluorophore as already stated. When it is irradiated with an excitation light Le, therefore, it emits a light different in wavelength from the excitation light, generally fluorescence. While the labeled sample plug is migrating inside the separation channel 16, therefore, the intensity of the fluorescence emitted when this sample plug is separated according to differences in size, electric charge and so forth, and reaches the detection region Po, and irradiated therein with the excitation light Le is plotted against the time required for the sample plug to reach the detection region Po. This is a so-called electropherogram (electrophoresis data) inherent to each sample plug.

A fluorescence detecting module 40 for detecting the fluorescence has a semiconductor light detecting element 20, which in the illustrated cross section appears to be a lateral pair. Actually, in a plan view, it is in the shape of a doughnut in which the excitation light Le to irradiate the sample passes through a central through hole 41 (generally in the form of a pinhole). When this excitation light Le impinges on the chip 10 transparent to the light and irradiates the sample in the separation channel 16 inside the detection region Po, the sample emits fluorescence Lf. Then, this fluorescence Lf is transformed by a microlens 61 for collecting the fluorescence preferably into nearly parallel rays and enters an optical filter 50 disposed on the incidence plane side of the semiconductor light detecting element 20. The optical filter 50 is generally configured as an optical interference filter formed by coating one surface side of a quartz glass 52 and is able to selectively transmit the fluorescence Lf in order to remove as much of the scattered excitation light Le as possible and allow just the fluorescence Lf to fall incident onto the semiconductor light detecting element 20. The fluorescence collecting microlens 61 may be formed integrally with the chip 10 by cast molding or may be formed on a special base plate 61', as partially depicted by an imaginary line, and bonded to the rear surface of the chip 10.

There is no particular limitation on the specific structure of the optical interference filter 50 or the semiconductor light detecting element 20, which may be an existing structure as found in the device according to this invention as described below. The semiconductor light detecting element 20 is preferably formed of a photodiode which is fabricated using a hydrogenated amorphous silicon (a-Si:H) as disclosed in the above Documents 1 and 2. An a-Si:H photodiode has various desirable characteristics, not only in the case of invoking an electrophoretic method, as enumerated in 1)-4) below.

1) A fluorescence band of fluorophores (such as, for example, Fluorescein, Green Fluorescence Protein, TOTO, and Ethidium Bromide) is located in a visible light region, in which the absorption coefficient of the a-Si:H is high.

2) Since a dark current of a-Si:H is several orders of magnitude lower than that of crystalline silicon, it has an advantage of obviating the need for cooling and achieving miniaturization.

3) A-Si:H permits pattern formation by the semiconductor microfabrication technology and a detector array to be readily manufactured.

4) A-Si:H is advantageous for mass production and an ease of cost reduction since it can be directly formed on an inexpensive glass or plastic substrates by using plasma enhanced chemical vapor deposition.

The present inventors actually fabricated an integrated a-Si:H photodiode as disclosed in Document 2 mentioned above and subjected this device to an experiment using an argon ion laser (488 nm) as an excitation light source, with the result that the limit of detection was found to be 17 nM for fluorescing concentration. The device manifested the highest detection sensitivity among the several examples of fluorescence detector of this sort reported to date. This device in fact has succeeded in analyzing microfluidic DNA fragments and enantiomers of amino acids.

A final target to be achieved by these fluorescence detector resides in the realization of a so-called lab-on-a-chip or micro total analysis system (=µTAS). That is, the goal is to integrate and miniaturize, on a single chip, all the elements and devices necessary for an analytic process, making possible "point-of-care" analysis. Some if not all of the concepts of the method of fluorescence detection analysis were indeed established prior to the disclosure of Documents 1 and 2 mentioned above. Actually in the case of the microfluidic electrophoresis, high-speed genotyping using 96 to 384 channels was carried out. Moreover, microfluidic valves and pumps were proposed and made available for enabling a large-scale parallel operation of microfluidic samples. As a result, it has now become possible to perform microfluidic cell sorting and combinatorial optimization for protein crystallization conditions in large scale integrated microchambers, utilizing such microfluidic valves or pumps.

Even prior to the disclosure of the Documents 1 and 2 mentioned above, analytical processes such as electrophoresis and the sample preparation processes had passed the point of being successfully integrated and miniaturized and enabled partially to undergo large scale integration. In most of these conventional devices, a laser-induced fluorescence detection system composed of a photomultiplier, a CCD, an optical interference filter, and a laser is used for high sensitivity microfluidic lab-on-a-chip analysis. This system can hardly be called a device suitable for freely portable "point-of-care" analysis. In this respect, the aforementioned system proposed by the present inventors has built a foundation for realizing "point-of-care" biochemical analysis with high speed and low sample consumption as recognized in the Documents 1 and 2 mentioned above. When this success is further developed to the point of the construction and practical realization of a lab-on-a-chip, the lab-on-a-chip will be useful enough for the prompt detection and identification of pathogens scattered by so-called bioterrorism, diagnosing genetic diseases, and performing stress monitoring and the like, and therefore can be expected to have a huge industrial impact.

What has become main problem in this respect is the deficiency in the degree of freedom of excitation light source selection and a lack of sufficient detection sensitivity. As already pointed out, as described in the above Document 2, an argon ion laser was used. Ultimate integration and miniaturization of the detection system cannot be expected with that laser, however. When a blue-green semiconductor laser (such as, for example, the Protera 488 made by Novalux Inc. or the Sapphire made by Coherent Corp.) using a SHG (second harmonic generation) element is used instead, it appears to be capable of realizing a compact fluorescence detection system including an excitation light source, which is necessary for a "point-of-care" microfluidic lab-on-a-chip. In fact, such a detection system is good enough for most biochemical analyses.

However, it is a fact that there is a need for a higher sensitivity detection technology in various areas, such as DNA and protein analysis. In fact, there is a demand for the limit of detection to be further reduced by an order of magnitude or more. When the laser light source of the kind mentioned above is used with the integrated a-Si:H fluorescence detector, the background photocurrent due to the scattered laser light is high and the noise level determines the limit of detection. This itself constitutes a problem common to integrated fluorescence detectors.

On the other hand, integration with surface emitting laser diodes, which can be readily arrayed and have good mass production capability, can be considered practical for realizing highly multiplexed bioanalysis. This point, however, is not discussed in detail in the above Documents 1 and 2. A search for candidates for surface emitting laser diodes which are usable herein revealed a ZnSe-based surface emitting laser diode that emits blue-green light suitable for biochemical analysis. This laser, however, can operate only at a low temperature of 77K and generally has a short life due to the high ionicity of ZnSe based material, so it cannot form a practical device.

In the case of GaN based material which is popularly used in a blue LED (light-emitting diode) and a blue-violet laser, use of this material in an optically pumped surface emitting laser has been reported. The current injected type, however, has technical problems regarding a reduction of P-layer resistance as well as a distributed Bragg reflection (DBR) mirror which is generally used to form a laser resonator and also poses a problem regarding the oscillation wavelength. At present, among current-injected surface emitting laser diodes with high reliability, it is the GaInAlP-GaAs surface emitting laser that generates light of the shortest wavelength, about 650 nm. This laser, however, imposes a limit on fluorophores which can be efficiently excited. It is incapable of exciting fluorophores useful for the biochemical analysis under discussion.

When the focus is just on the point of using a surface emitting laser diode, a fluorescence detector in which an optical interference filter, a GaAs photodiode and AlGaAs surface emitting laser diode are monolithically integrated on a GaAs substrate as disclosed in Document 3: E. Thrush et al., "Integrated bio-fluorescence sensor," J. of Chromatography A, Vol. 1013, (Sep. 26, 2003), pp. 103-110, has been already disclosed. In this device, the optical interference filter is the distributed Bragg reflection mirror used in the GaAs based surface emitting laser diode. Thus, the device is composed wholly of the GaAs based material. It is, therefore, advantageous for manufacturing due to entirely the same technique as that of the already mature GaAs based surface emitting laser diodes. Also, it is suited to highly multiplexed biochemical analysis. From the contents disclosed in Document 3, however, the limit of detection and the like are not clear. In fact, as yet there has been no biochemical analysis using such a device. Since the laser diode is composed of GaAs based material, its emission wavelength is of course in the near infrared region (773 nm). Though in principle this wavelength is advantageous for suppressing Rayleigh scattering, it is incapable of exciting fluorophores useful for biochemical analysis such as fluorescein, green fluorescence protein, or TOTO.

This invention is accomplished in the light of the above state of affairs, and is aimed at providing a fluorescence detector which is freed of the restriction on the wavelength of the excitation light emitted by an excitation light source, namely, it increases the selection freedom of the excitation light sources that can be used, effectively excites fluorophores to be used in various kinds of biochemical analysis, detects fluorescence with high sensitivity, and offers a fundamental platform indispensable to finally realizing a lab-on-a-chip.

The description made thus far has been directed toward the detection of fluorescence emitted from a fluorophore. Recently, instead of an organic molecular fluorophore as a fluorescence marker for biochemical analysis, a semiconductor quantum dot has attracted particular attention because it is advantageous for providing a broad enough absorption spectrum to permit selection freedom of excitation light sources as well as a narrow fluorescence spectrum suited to wavelength-multiplexed analysis and entailing only small photobleaching. As stated in the beginning part of this specification, this invention is aimed also at providing a device which is capable of coping with this new fluorescence marker. It is further aimed at providing a device which is suitable not only for the detection of fluorescence but also for the detection of phosphorescence whose peak wavelength is generally located at a longer wavelength than that of fluorescence. Thus, the fluorescence and the phosphorescence which are emitted from a micro-object in consequence of the irradiation of an excitation light are collectively conceived as the emission light from the micro-object.

SUMMARY OF THE INVENTION

In order to achieve the object described above, the present inventors propose as a first aspect of the invention a micro-object emission light detecting device for detecting with a semiconductor light detecting element emission light emitted in the form of fluorescence or phosphorescence from a micro-object irradiated by excitation light emitted from an excitation light source, characterized by comprising a converging microlens inserted partway along a light path of the excitation light to converge the excitation light and irradiate the micro-object with light of an elevated optical density and induce the micro-object to generate emission light from two-photon absorption.

A second aspect of this invention is directed toward providing a micro-object emission light detecting device for detecting with a semiconductor light detecting element emission light emitted in the form of fluorescence or phosphorescence from a micro-object irradiated by excitation light emitted from an excitation light source; characterized by comprising a micro-resonator constituted by a pair of mirrors inserted partway along a light path of the excitation light; having the micro-object disposed between the pair of mirrors; and utilizing the multiple reflection function of the micro-resonator to elevate the effective intensity of the excitation light and irradiating the micro-object with the excitation light of elevated intensity to thereby induce the micro-object to generate emission light from two-photon absorption.

Here, the pair of mirrors that form the micro-resonator may typically be distributed Bragg reflection mirrors and the light path between the excitation light source and the micro-resonator may be provided partway along the length thereof with a converging microlens for converging the excitation light and, in addition thereto, with a concave lens for causing the converged excitation light to be paralleled and injected into the micro-resonator.

A third aspect of the invention is directed toward providing a micro-object emission light detecting device for detecting with a semiconductor light detecting element emission light emitted in the form of fluorescence or phosphorescence from a micro-object irradiated by excitation light emitted from an excitation light source; characterized by comprising a Q switch laser that generates a short pulse laser in response to the irradiation with the excitation light and elevates the peak light intensity instantaneously, and irradiating the micro-object with the short pulse laser beam as an excitation light to have the micro-object generate emission light from two-photon absorption.

Unlike the first~third aspects of the invention, a fourth aspect of this invention which is capable of accomplishing the objects mentioned above by utilizing ordinary one-photon absorption is directed toward providing a micro-object emission light detecting device for detecting with a semiconductor light detecting element emission light emitted in the form of fluorescence or phosphorescence by a micro-object irradiated by excitation light emitted from an excitation light source; characterized by comprising an SHG element inserted into the resonator disposed partway along a light path of the excitation light for the purpose of efficiently doubling frequency of light from the excitation light source and, by irradiating the micro-object with the frequency doubled light, enabling the micro-object to generate emission light from one-photon absorption.

When the two-photon absorption is utilized as in the first~third aspects of this invention, a more specific limitation is that preferably the wavelength of the excitation light is greater than the wavelength corresponding to the band gap of the semiconductor light detecting element, and the wavelength of the emission light is smaller than the wavelength corresponding to the band gap of the semiconductor light detecting element, and, particularly, that the excitation light has a wavelength that falls in the near infrared region.

The emission light generated from the micro-object is preferably impinged on the semiconductor light detecting element through an optical filter possessing selective transmittance to the emission light. In addition to this condition, at least the part of the side wall of the optical filter and the semiconductor light detecting element on which the scattered light of the excitation light may fall incident should be covered with a shielding layer.

Structurally, preferably the emission light detecting module provided with the semiconductor light detecting element and the optical filter mentioned above assumes a circular form in a plan view or a solid polygonal shape having n vertices, wherein n denotes an integer of not less than 3, the solid form has in a part thereof a circular through hole or polygonal through hole with n vertices, and the excitation light passes through this through hole. In this case, it is most general to have the emission light detecting module assume a circular form in a plan view and the through hole assume a circular form so that they together assume the shape of a doughnut.

Further, the converging microlens may be provided on the substrate on which the semiconductor light detecting element is formed or provided on the light-transparent chip on which the micro-object is disposed.

From the viewpoint of structural simplification, preferably the semiconductor light detecting element is integrated with the light-transparent chip on which the micro-object will be disposed. From the viewpoint of disposing all the relevant components in parallel, it is preferable to have the excitation light source and the semiconductor light detecting element integrated on the same substrate. Of course, the converging microlens may also be optionally integrated on this substrate.

In this case, it is advantageous for the excitation light source to be a surface emitting laser diode and for the semiconductor light detecting element to be a photodiode or a photoconductor fabricated using the a-Si:H material.

Further, when the combination of the semiconductor light detecting element and the excitation light source is regarded as one module, a device is useful in which a plurality of such modules are arranged in one dimension or in two dimensions to form a module array. When a scanning mechanism is provided for scanning the modules or the module array in one-dimension, two-dimensions, or, further, three-dimensions, such a device gives rise to various applications.

The design to divide the semiconductor light detecting element into a plurality of parts and impinging the emission light generated by the micro-object on the divided parts of the semiconductor light detecting element via the optical filters provided with different spectral characteristic properties permits wavelength multiplexed analysis.

According to the first~third aspects of this invention mentioned above, a micro-object such as a fluorophore or a semiconductor quantum dot, or a micro-sample labeled with a fluorophore or a semiconductor quantum dot, is excited to generate fluorescence or phosphorescence when irradiated with excitation light due to two-photon absorption. Therefore, when the micro-object is made to emit the emission light in a visible light region and an a-Si:H photodiode is preferably used as the semiconductor light detecting element, the wavelength of the actual excitation light is twice as long as the wavelength in the case of not using the principle of two-photon absorption. When the optical absorption peak of the micro-object has a wavelength of about 500 nm, for example, it is possible to use an excitation light source which is capable of generating a light with a wavelength of about 1000 nm. This fact markedly increases the selection freedom of the excitation light source and, consequently, permits selection from among various existing semiconductor excitation light sources having high stability and marked convenience of use. The wavelength relationship mentioned above conforms to the aforementioned relationship of the wavelength of the excitation light being greater than the wavelength corresponding to the band gap of the semiconductor light detecting element and the wavelength of the emission light being smaller than the wavelength corresponding to the band gap of the semiconductor light detecting element, and particularly that the wavelength of the excitation light is in the near infrared region expands the number of selectable semiconductor excitation light sources, making it possible to stable ones.

For the semiconductor light detecting element, the adoption of a-Si:H-based material is most desirable as mentioned above. More generally, for a light detection system using the semiconductor material, it is very useful to induce two-photon absorption. The absorption coefficient of a semiconductor increases as the energy is increased. In the case of ordinary one photon absorption, since the wavelength of the excitation light is always smaller than the wavelength of the emission light, inevitably the absorption coefficient of the semiconductor light detecting element at the wavelength of the excitation light becomes greater than the absorption coefficient at the wavelength of the emission light. When leakage of the excitation light, such as by scattering, into the semiconductor light detecting element is considered, the SN ratio (signal-to-noise ratio) tends to decline since the sensitivity to the excitation light or the scattered light thereof is higher and the sensitivity to the emission light from the micro-object is lower. On the other hand, the excitation owing to the two-photon absorption fortunately reverses this relation, namely the SN ratio can be increased in principle because the absorption coefficient of the semiconductor light detecting element is lower at the wavelength of the excitation light and is higher at the wavelength of the emission light.

In other words, even by appreciably heightening the optical density of the excitation light for the purpose of inducing the two-photon absorption, it is possible to diminish greatly the possibility that the sensitivity of the semiconductor light detecting element will be degraded due to the background photocurrent.

Further, as recognized in the aforementioned configuration of this invention, the two-photon absorption can be induced efficiently by using a converging microlens, a micro-resonator, or a Q switch short pulse laser beam having a high peak intensity. Using a converging microlens makes it possible to selectively excite the region in the vicinity of the focal point, which is similar to spatial filtering used in a confocal fluorescence detection system and, even in this sense, to diminish the background light.

Among the kinds of laser light scattering, Rayleigh scattering can be lowered to $(1/2)^4 = 1/16$ when the wavelength of the excitation light is doubled. In this respect too, it is highly effective to use longer wavelength light as the excitation light.

According to the fourth aspect of this invention instead of two-photon absorption, frequency-doubled excitation light having sufficient optical intensity can be obtained due to a SHG element being incorporated in the resonator structure, which is capable of irradiating the sample-plug. Furthermore this allows for the use of a technically mature existing semiconductor excitation light source.

Further, when the emission light emitted by the micro-object is to impinge on the semiconductor light detecting element via the optical filter possessing selective transmittance to the emission light in accordance with the specific embodiment of this invention, noise is further diminished and the sensitivity is consequently greatly elevated by covering with a shielding layer at least the part of the side wall of the optical filter and the semiconductor light detecting element on which scattered light of the excitation light may fall incident.

According to this invention, which not only brings an advantage in terms of performance as described above, but also brings the realization of a lab-on-a-chip much closer by increasing the selection freedom of the excitation light source that is used, solving the problem of material compatibilities in the combination, and facilitating integration with the light detecting element.

In particular, an a-Si:H emission light detecting module combined with the surface-emitting laser diode according to the specific mode of this invention has excellent mass-production capability and enables costs to be reduced and, therefore, it is believed that it will play a great role in highly multiplexed parallel biochemical analysis.

Since this invention is based on the structural principle described above, it does not need to be limited to analysis using electrophoresis but may be applied to a wide range of bioanalysis due to the great improvement in the limit of detection. It is capable of providing an extremely effective means for realizing all types of microfluidic lab-on-a-chip based on fluorescence detection, and can also be applied to fluorescence detection systems such as DNA microarrays and protein microarrays. It is thought to be applicable to DNA fragment sizing analysis, DNA sequencing, Polony sequencing, RNA analysis, protein separation, amino acid analysis, cell sorting, drug screening, and so forth. Furthermore, when combined with a microfluidic PCR-electrophoresis device, it is effective for "point-of-care" detection and identification of pathogens and bacteria that can be used to decompose oil.

Particularly when a semiconductor quantum dot is used instead of a fluorophore as in DNA microarray analysis in which the large mass thereof poses no appreciable obstacle, it is decisively effective in the detection of fluorescence or the detection of phosphorescence due to the magnitude-larger two-photon absorption cross section of the semiconductor quantum dot.

Further, when the combination of the excitation light source and the semiconductor light detecting element is formed as a module and such modules are disposed in a one-dimensional or two-dimensional array in accordance with the specific mode of this invention, its applicability is further extended. When the individual modules or module arrays can be scanned in one-dimensionally, two-dimensionally or three-dimensionally, the range of application is further widened. Such modules or module arrays are effective not merely for parallel analyses but also for micro-object imaging and the like, owing to the aforementioned effect of spatial filtering of the two-photon absorption.

BRIEF EXPLANATION OF THE DRAWING

FIG. 3 is a schematic diagram of a fluorescence detecting device as a second embodiment of this invention.

DESCRIPTION OF THE PREFERRED EMBODIMENT

Figure 1:
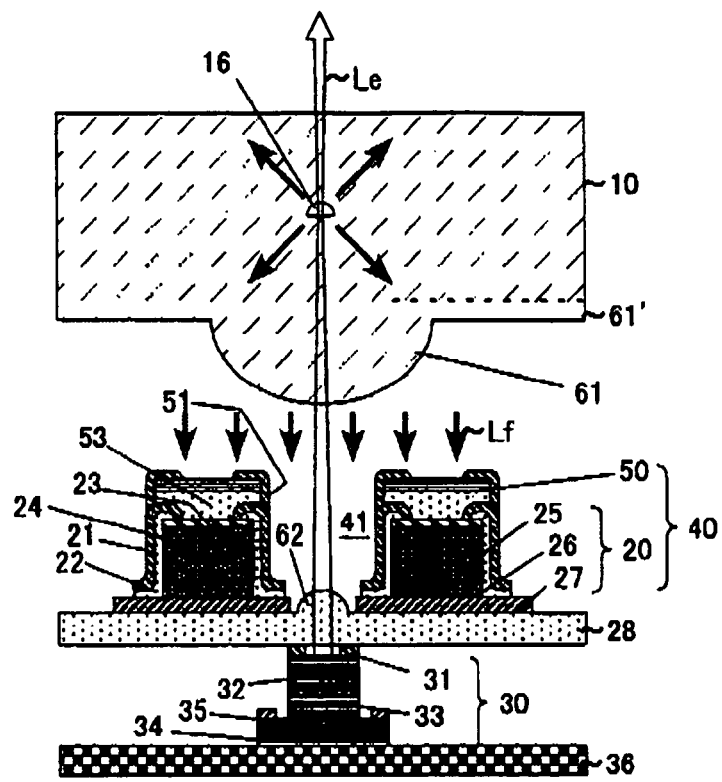
FIG. 1 a schematic diagram of a fluorescence detecting device as an embodiment of this invention.
Figure 10:
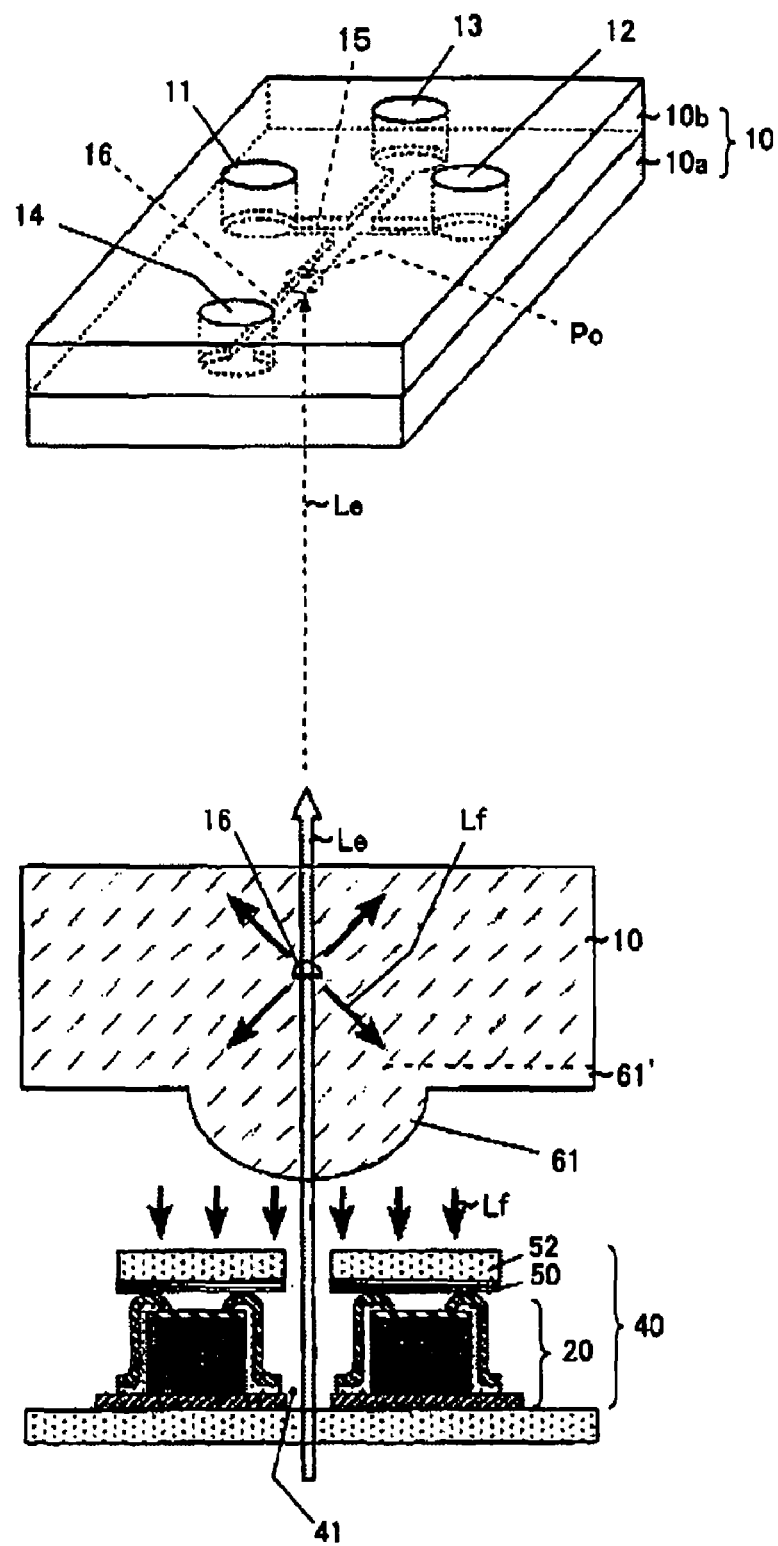
FIG. 10 is a schematic diagram of one example of a conventional fluorescence detecting device.

FIG. 1 illustrates one preferred embodiment of this invention. As regards the reference numerals affixed to the component elements of the conventional example already described with reference to FIG. 10 and the reference numerals used in the other diagrams, the identical reference numerals denote identical or similar component elements. Concerning the component elements, the contents already explained somewhere, are applicable elsewhere with unless otherwise specified, repeated explanation thereof may be avoided.

The embodiment of this invention shown in FIG. 1 is assumed to have been configured so as to be applied to the electrophoretic analysis already described. The micro-object which generates fluorescence in this case as emission light resulting from irradiation with an exciting light Le, therefore, is a sample plug (not illustrated) labeled with a fluorophore and passing through a separation channel 16 in a chip 10 composed of glass or plastic substrate as already described.

The excitation light Le is a light which is generated by a surface-emitting laser diode 30 selected as an excitation light source in the present mode of embodiment. For the sake of convenience, the explanation of the surface emitting laser 30 will be deferred, and the explanation will be started from the side of a fluorescence (emission light) detecting module 40 on which a fluorescence Lf emitted in response to irradiation with the excitation light Le impinges after it has been paralleled via a fluorescence collecting microlens 61 already explained with reference to the conventional example. A semiconductor light detecting element 20 in the fluorescence detecting module 40 is preferably an a-Si:H photodiode 20 composed of an a-Si:H material. Generally, a device-grade a-Si:H film can be fabricated even at a low temperature of about 200° C. by plasma decomposition of an $SiH_4$ gas or a hydrogen-diluted $SiH_4$ gas and having the generated active species grow on a substrate (plasma enhanced chemical vapor deposition). The impurity doping is done merely by adding an impurity gas such as $B_2H_6$ or $PH_3$ to the source gas, resulting in a P type and an N type a-Si:H respectively.

Due to this low-temperature process, the a-Si:H photodiode can be directly formed on an inexpensive substrate such as glass or plastic. The illustrated embodiment assumes such a case. However this invention does not need to specify particularly the structure of the a-Si:H photodiode 20 itself but may adopt any of the known existing structures. Here, the procedure to fabricate the illustrated photodiode will be described briefly.

A bottom electrode 27 is formed by sputtering an appropriate conductive material such as chromium on a transparent substrate 28, for example, a glass substrate 28. The sequential deposition of an N type a-Si:H film 26, an intrinsic a-Si:H film 25, and a P type a-Si:H film 24 thereon is followed by the deposition of top transparent conductive electrode 23, for example, ITO. The patterning of the a-Si photodiode 20 including an electrode is done at a suitable time by photolithography so as to make the photodiode an annular shape containing a through hole (pinhole) 41 at its center. The pinhole in the bottom electrode 27 in this manner acts as an aperture for the excitation light Le.

The side wall of the PIN photodiode 20 as described above is covered with an appropriate insulating film 22 such as SiN, and is then covered with an appropriate metal film 21 such as aluminum. This metal film 21 is electrically connected to the top transparent conductive film 23 to form an electrode opposite the bottom electrode. The deposition of an insulating film 53 such as SiN or SiO on this a-Si:H photodiode 20 is followed by CMP (chemical mechanical polishing) to flatten the surface and an optical filter 50 is then formed thereon. The optical filter 50 is ordinarily formed as an optical interference filter. The optical interference filter 50 is formed, for example, of $ZnS/YF_3$ or the like. The fabrication of this optical interference filter with selective transmittance (blocking the excitation light Le) to the fluorescence Lf has been well known and is arbitrarily applicable to this invention. Thus, the detail thereof will be omitted from the description here.

The present embodiment according to an aspect of this invention is characterized in that the side wall of the optical interference filter 50 is covered with a shielding film 51. The material of this insulating film 51 is arbitrary, being only required to block the excitation light to the fullest possible extent, and may be a coating film that blocks the light. It may even be a metal film; selecting aluminum, the same material used for the electrode of the photodiode 20, is convenient in terms of the fabrication process. The shielding layer 51 thus provided, together with the metal electrode 21, to cover the side wall of the photodiode 20 prevents scattered excitation light from impinging on the photodiode 20 via the side wall of the optical filter, particularly the inner wall of the pinhole 41. This provides a major effect in improving the SN ratio.

Preferably, at the back of the substrate 28 on which the photodiode 20 is fabricated, a vertical cavity surface emitting laser diode 30 (VCSEL) is integrally formed. The structure of the surface-emitting laser 30 may be any known to the art.

To explain an example of the general configuration with reference to the illustration, the layer structure on substrate 36 comprises an N-type distributed Bragg reflection (DBR) mirror 34, an active layer 33 with a quantum well, a P-type distributed Bragg reflection mirror 32, and electrodes 31 and 35 disposed at the opposite ends in the direction of the electric current, which are fabricated by metal-organic chemical vapor deposition (MOCVD) or molecular beam epitaxy.

The carriers from the pair of electrodes 31 and 35 that are injected via the N-type distributed Bragg reflection mirror 34 and the P-type distributed Bragg reflection mirror 32, recombine in the active layer 33, and emit light (occasionally forming an electrode directly on the active layer). At this time, the two distributed Bragg reflection mirrors form a resonator which promotes stimulated emission.

Generally, the distributed Bragg reflection mirrors are formed of about 20-30 cycles of AlAs/GaAs layers. The N-type distributed Bragg reflection mirror 34 is doped with an Se impurity while the P-type distributed Bragg reflection mirror 32 is doped with a Zn impurity.

In order to generate light with a wavelength of about 980 nm, for example, the active layer 33 of a surface-emitting laser diode can be given a $Ga_{(1-x)}In_xAs/GaAs$ quantum well structure (x=about 0.2). Furthermore, current confinement by selective wet oxidation of the AlAs layer is preferably done by forming a mesa structure with a reactive ion beam or the like. Since the AlO layer has a low refractive index, a wave guide structure having a GaAs/AlAs region as a core and a GaAs/AlO region as a clad is obtained. Therefore, this structure is capable of realizing current confinement and optical guiding simultaneously. Such a structure is important as a highly efficient low threshold laser diode and is well known.

In fabricating the device of this embodiment, the process for fabricating the surface-emitting laser diode 30 on an appropriate substrate of GaAs or the like and the process for fabricating a fluorescence detecting module comprised of the photodiode 20 and the optical filter 50 can be done independently of each other. Thus, the excitation light source and the fluorescence detecting module can be integrated by the combination of materials mentioned above. This is of course desirable for realizing a highly portable lab-on-a-chip.

While the individual elements except for the shielding film 51 provided by the present inventors' originality so as to cover the side wall of the optical filter 50 may already exist, the characteristic structure of this invention is recognized in the presence of a converging microlens 62 disposed partway along the light path of the excitation light for the purpose of converging the excitation light. This converging microlens 62 is so adapted as to have the focal point thereof fall on the micro-object emitting fluorescence when irradiated with the excitation light Le (the sample plug in the separation channel 16, in the present mode of embodiment) or at least in the vicinity thereof. Particularly in the present embodiment, the converging microlens 62 is provided integrally on the glass substrate 28 on which the photodiode 20 is formed, and is located in the pinhole 41 portion. This is because it can readily be formed by cast molding when the substrate material is glass as described above.

Recently, microlenses of semiconductor and glass material can be arbitrarily formed by semiconductor microfabrication techniques utilizing the reflow of photoresist, for example. Thus, they may be fabricated by convenient techniques, depending on the selected substrate materials. Of course, cast molding and other such convenient techniques are available when a plastic substrate is used.

In any case, so long as the converging microlens 62 is provided in accordance with this invention, the excitation light Le, for example, near infrared light with a wavelength of about 980 nm, emitted by the surface-emitting laser 30 can be converged by converging microlens 62 and irradiate the sample-plug migrating in the separation channel 16 with higher optical density. Thus, even a fluorophore with an absorption peak at a wavelength smaller than that of the excitation light Le, or a micro-object labeled with such a fluorophore, can be excited, owing to the two-photon absorption, with an energy effectively equivalent to a wavelength of 490 nm, one half of the wavelength of the excitation light. In fact, a fluorophore excited by the two photons of the near infrared light emits visible fluorescence.

The generated fluorescence is collected and substantially paralleled by the fluorescence collecting microlens 61, impinges substantially perpendicularly on the optical interference filter 50 to remove the excitation light component, then impinges on the a-Si:H photodiode 20 and subjected therein to photoelectric conversion. Generally, for the sake of optimizing the carrier collection efficiency, usually a reverse bias in the order of several volts is applied to the a-Si:H photodiode 20.

The transition probability for such two-photon absorption is proportional to the square of the light intensity. Thus, the convergence of the laser beam by the microlens 62 formed on the glass substrate 28 in the present embodiment has an extremely large effect. This is advantageous in that the two-photon absorption can be realized with a relatively lower laser power, and in that the vicinity of the focal point (the vicinity of the micro-object) alone can be selectively excited, enabling spatial filtering close to the confocal fluorescence detection system and reducing background light. Among laser light scattering, Rayleigh scattering can be lowered to $(1/2)^4=1/16$ because the wavelength of the excitation light Le can be doubled.

As already explained, in the case of ordinary one-photon absorption, since the wavelength of the excitation light is always smaller than that of the fluorescence, the absorption coefficient of the semiconductor light detecting element at the wavelength of the excitation light is always higher than that at the wavelength of the fluorescence and therefore inevitably lowers the SN ratio, whereas two-photon absorption can substantially invert this relationship. Particularly when the wavelength of the excitation light is larger and the peak wavelength of the fluorescence band is smaller than the wavelength corresponding to the band gap of the semiconductor light detecting element, the absorption coefficient of the semiconductor light detecting element at the wavelength of the fluorescence band becomes much larger than that at the wavelength of the excitation light, which is advantageous for fluorescence detection with high sensitivity.

In the case of a-Si:H, the band gap thereof, namely the optical energy gap Eo (the so-called Tauc gap) corresponding to the band gap in an ordinary crystalline semiconductor, is typically about 1.7 eV which corresponds to a wavelength of about 730 nm. When the wavelength of the excitation light is set at 980 nm, the relationship mentioned above is satisfied because this wavelength is sufficiently greater than the wavelength corresponding to the Eo while the fluorescence wavelength of the fluorophore excited by the two-photon absorption is only some tens of nm longer than a wavelength of 490 nm that is one half of 980 nm, and thus becomes sufficiently smaller than the wavelength corresponding to the Eo.

Figure 2:
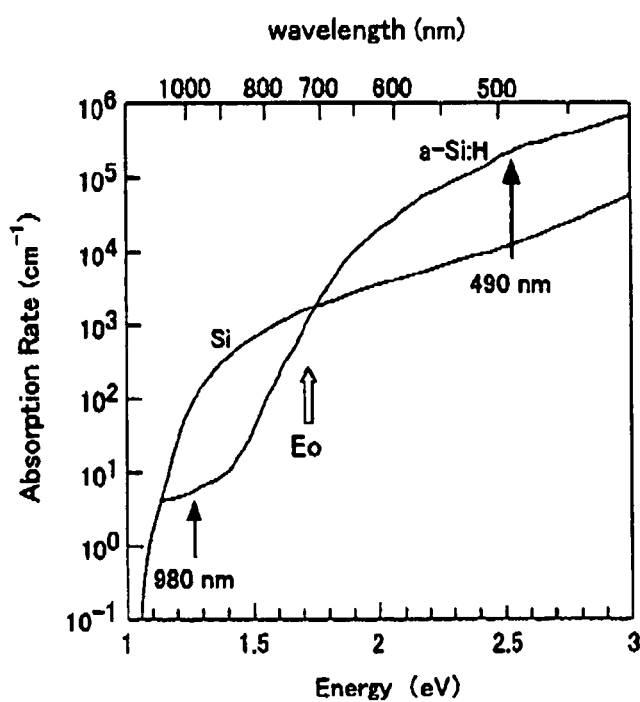
FIG. 2 is an optical absorption spectrum of a-Si:H which can be used to fabricate a photodiode.

A look at the characteristic diagram shown as FIG. 2 allows a full understanding of this situation. Among other points deserving attention and individually indicated with an arrow mark, the absorption coefficient of the a-Si:H is decreased by four orders of magnitude from the visible light region above the optical energy gap Eo to the near infrared region below the Eo (from a wavelength of 490 nm to a wavelength of 980 nm, for example). That is, if the excitation light Le leaks into the photodiode 20 in the present embodiment, the sensitivity thereof will be amply lower than the sensitivity relative to the wavelength of the fluorescence. Conversely, therefore, when the excitation light intensity Le is increased to realize the two-photon absorption, background photocurrent caused by laser scattered light can be greatly decreased, which can be expected to greatly improve the sensitivity.

By using a configuration in which the photodiode 20 and the side wall of the optical interference filter 50 is shielded by the shielding film 51 and the electrode 21, as in the present embodiment, the SN ratio can be further improved, and in fact a major improvement in sensitivity is observed. When an anti-reflection coating is suitably applied to the surfaces of the chip 10, the microlens 61, the glass substrate 28, and the surface-emitting laser diode 30, though not illustrated, it is effective in reducing background photocurrent caused by the laser scattered light.

The structures 51 and 21 for the shielding may be substantially required only on the surfaces which face the light path of the excitation light Le. That is, only portions of side walls on which scattered light of the excitation light Le may impinge need to be covered with the shielding film 51 or the electrode 21. In the illustrated case, for example, the electrode 21 requires an outer peripheral part for the purpose of making electrical contact with an external component but the shielding film 51 does not require an outer peripheral part, so application on just the inner side wall facing towards the pinhole 41 is enough. However, from the fabrication standpoint, providing the shielding structure on both the inner and outer side walls of the photodiode 20 and the optical interference filter 50 in one operation produces a more complete shielding property for the same amount of time and labor.

While in the illustrated embodiment, the fluorescence detecting module is constituted geometrically in the form of a doughnut having a through hole or pinhole 41 in the center thereof through which the excitation light Le passes, application of this invention is not limited to just that structure. Even when the excitation light source 30 and the fluorescence receiving element 20 are simply disposed in parallel, for example, it is possible to incorporate of the converging microlens 62 which serves to induce the two-photon absorption. This point holds good with the other embodiments of this invention described below.

Further, the doughnut form does not need to be limited to a circular shape. The fluorescence detecting module 40 is only required to be formed in a solid shape that surrounds the through hole. The fluorescence detecting module 40 can be formed in the shape of a quadrilateral shape or other polygonal shape having n vertices ($n \geq 3$) as seen from a plan view, with a through hole 41 of a circular shape or a polygonal shape with n vertices opened in a part thereof (generally at the center), for the excitation light Le to pass therethrough.

The utility of the fluorophore excitation by the use of two-photon absorption according to this invention, namely the reduction of the background photocurrent and the spatial selectivity of light excitation, naturally functions effectively not merely in the case of using the surface-emitting laser diode 30 but also in the case of using a conventional edge-emitting laser diode. In the fluorescence detecting device illustrated in FIG. 1, the surface-emitting laser diode 30 may be substituted with a conventional semiconductor laser, and the structural contrivance illustrated in FIG. 3 enables the fluorescence detecting device of this invention to be provided as a device of a still lower cost.

When the micro-object is a sample plug in electrophoresis, for example, since the chip 10 made of glass or plastic is used as already explained, the use of the a-Si:H photodiode 20 as the semiconductor light detecting device allows this chip 10 to be used as the structural substrate for the fluorescence detecting module. In the illustrated case, first the optical filter 50 is provided on the back of the chip 10, after which, in accordance with the usual fabrication method, deposition of the insulating film 53 is followed by the deposition of the transparent electrode 23 and the formation of the photodiode 20 which may have the same construction as described in the above. The electrode 27 corresponding to the electrode 27 which is formed as a bottom electrode in the embodiment of FIG. 1 constitutes part of the shielding structure 21 covering the side wall of the photodiode 20 in the present embodiment. This configuration is similar to that of the embodiment illustrated in FIG. 1 in that the shielding film 51 is formed preferably at least on the inner side wall of the optical filter 50 facing the pinhole 41, and is generally formed on the outer side wall. The overall shape is also assumed to be that of a doughnut. Only in the present embodiment, for the shielding film 51, a conductive material such as metal is used because it is required to make electric contact with the transparent conductive film 23. This shielding film 51 is to be used to form part of one of the electrodes of the photodiode 20.

Conveniently, in the present embodiment, the converging microlens 62 for converging the excitation light Le is obtained by processing the back surface of the chip 10 at the location inside the pinhole 41. From the standpoint of fabrication method, this is clearly advantageous. Similarly, it is possible to form the micro-converging lens 62 on the top of the chip 10 in the illustration and to inject excitation light Le from the side opposite the semiconductor light detecting element 20 across the chip 10. In the case of either structure, for the optical filter 50 a material such as for example SiO/TiO or the like has to be used that can withstand the a-Si:H deposition temperature of 200° C.

Further, the microlens 61 which is used in the mode of embodiment of FIG. 1 to collect the fluorescence is not needed in the mode of embodiment shown in FIG. 3. When the thickness of the chip 10 below the separation channel 16 is sufficiently small, it is possible to collect enough light even if the light receiving area of the semiconductor light detecting element 20 is small. This is because a structure called a proximity effect lens is incorporated without requiring use of a lens as a separate component. This configuration can constitute an important example of a structure for elevating the degree of integration.

Instead of directly on the back surface of the chip 10, the converging microlens 62 may be formed on a separate substrate 62' as shown up to one part by an imaginary line, and this substrate 62' may be affixed to the back surface of the chip 10. The converging microlens 62 may be formed as a separate member as shown by an imaginary line 62" in the illustration, provided at an appropriate location partway along the light path of the excitation light Le. This point may also be done in the embodiment illustrated in FIG. 1 and in the other embodiments described below.

It is also possible to use a graded refractive index lens with a planar shape (SELFOC lens). When a proximity effect lens is used, since there is a wide incidence angle distribution of the laser scattered light and the fluorescence falling incident on the optical filter 50, there are cases in which it is desirable to use as the optical filter 50 an optical absorption filter such as a color glass filter in place of the optical interference filter or to use a combination of the optical absorption filter and the optical interference filter. When multiple channels are analyzed in parallel, the use of a scanner or the like may be necessary.

The a-Si:H thin film not only can be directly formed on an inexpensive substrate such as glass or plastic as already described, but also can be integrated on a different substrate, such as GaAs. This originates from the fact that the fabrication process is as low as 200° C. and lattice matching does not matter because of the amorphous structure. Thus, the structure shown in FIG. 4 can be easily obtained. Specifically, both the excitation light source 30 and the semiconductor light detecting element 20 can be monolithically integrated on the same substrate 36 such as, for example, a GaAs substrate 36. In the illustrated embodiment, the surface-emitting laser 30 is formed on the substrate 36 in the central through hole 41 of the semiconductor light detecting element having the shape of a doughnut. The internal structures of the individual elements may be the same as described heretofore, and will be given no repeated explanation. As already described above, like reference numerals indicated in the diagrams of other modes of embodiment, denote identical or similar components.

The converging microlens 62 which is one of the characteristic structures of this invention may be provided on the top of the microlens 61 used for collecting fluorescence as illustrated in the present illustration, by utilizing the semiconductor microfabrication technology. As mentioned, it may be a graded refractive index lens, a spherical convex lens, or an aspherical convex lens as occasion demands. From among these lenses, a lens convenient from the standpoint of fabrication or convergence may be suitably selected.

Figure 4:
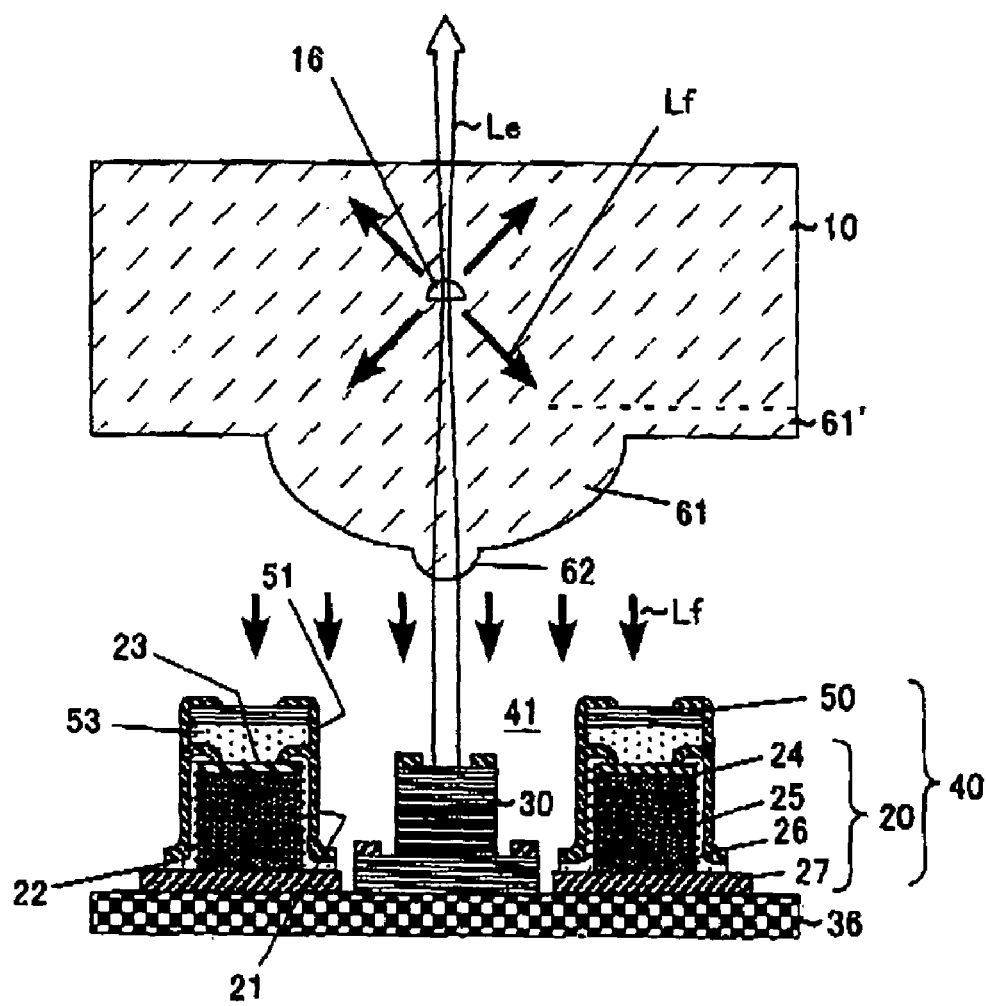
FIG. 4 is a schematic diagram of a fluorescence detecting device as a third embodiment of this invention.
Figure 5:
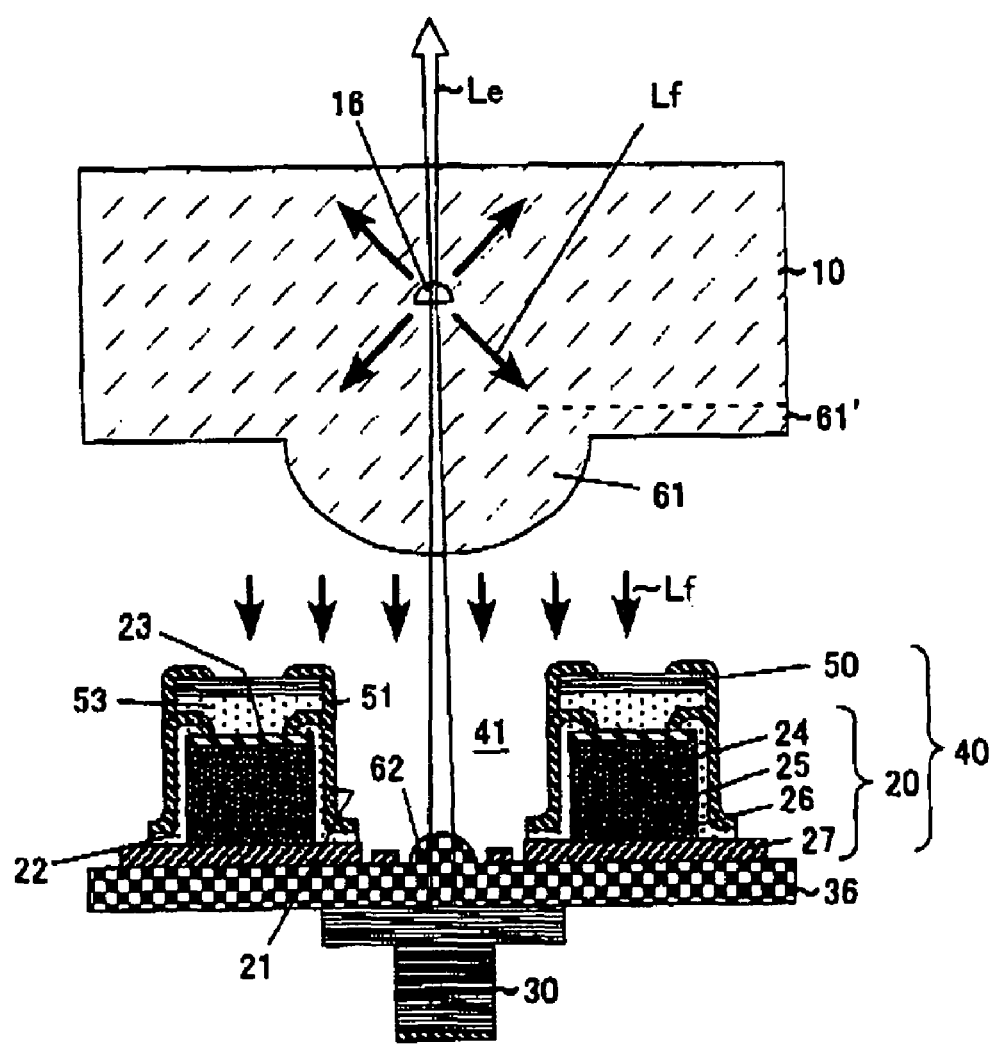
FIG. 5 is a schematic diagram of a fluorescence detecting device as a fourth embodiment of this invention.

The GaAs substrate 36 is transparent to near infrared light such as a wavelength of 980 nm. Thus, the surface-emitting laser diode 30 may be monolithically integrated on the back of the a-Si:H photodiode 20 across the GaAs substrate 36 as illustrated in FIG. 5. The converging microlens 62 may of course be fabricated in the through hole 41 on the other surface of the GaAs substrate 36 (on the surface on which the a-Si:H photodiode 20 is provided) at the position of the surface-emitting laser diode 30, as illustrated. The converging microlens may be made not only on the substrate but also on the top of the fluorescence collecting microlens 61, which is not illustrated herein. Since doing so makes it possible to readily increase numerical aperture of the converging microlens for converging the laser beam, the excitation volume can be decreased and the effective optical intensity increased, enabling realization of the two-photon absorption with a lower power. In any case, the monolithic integration of the surface-emitting laser diode 30 and the photodiode 20, as illustrated in FIG. 4 and FIG. 5, provides good productivity and enables costs to be reduced.

Figure 6:
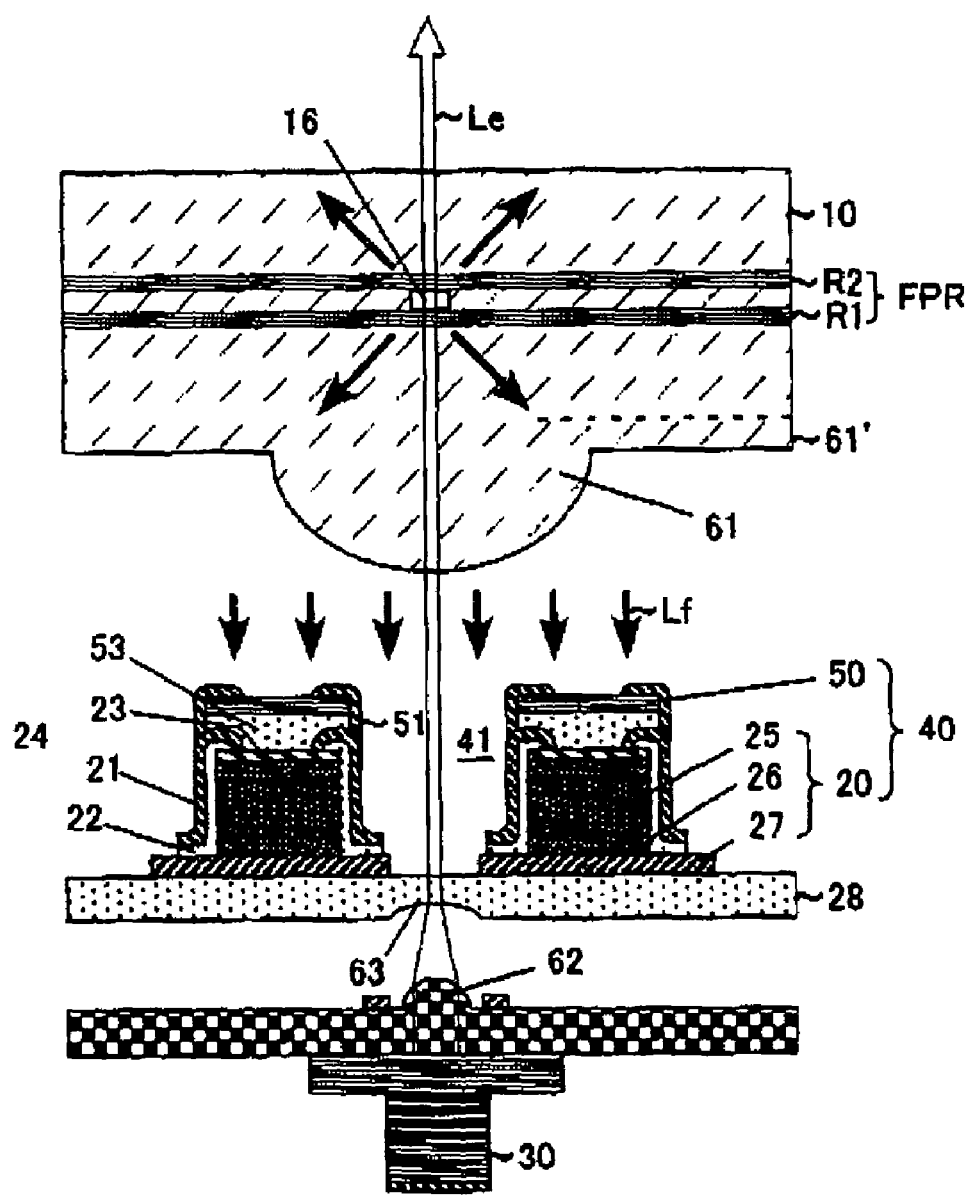
FIG. 6 is a schematic diagram of a fluorescence detecting device as a fifth embodiment of this invention.

This invention can further provide a structure with a micro-resonator FPR comprised of a pair of mirrors R1 and R2 that sandwich separation channel 16 therebetween, as illustrated in FIG. 6. Preferably, the pair of mirrors R1 and R2 are typically distributed Bragg reflection mirrors, and in terms of material, desirably may be a dielectric multilayer film.

When the sample plug in the separation channel 16 located inside the micro-resonator FPR is irradiated with the excitation light Le from the surface-emitting laser 30 preferably converged by the converging microlens 62 and further preferably substantially paralleled by a concave lens 63, multiple reflection of the excitation light Le occurs between the pair of mirrors R1 and R2 of the micro-resonator FPR. Then, by adjusting the wavelength of the excitation light Le so as to satisfy the resonance conditions by varying the temperature and the injection power of the surface-emitting laser diode 30, it is possible to greatly increase the optical intensity inside the micro-resonator FPR and thereby greatly elevate the probability of inducing the two-photon absorption.

In fact, according to an experiment conducted by the present inventors, the effective optical intensity in the micro-resonator FPR was found to be 325 times higher than when there was no micro-resonator FPR, whereby the probability of two-photon absorption also increased by 10000 times or more, when the reflectance of the mirror R1 positioned on the lower side in the illustration is set at 0.96, the transmittance at 0.04, and the reflectance of the mirror R2 on the upper side at 0.996.

The mirrors R1 and R2 used in this configuration may be distributed Bragg reflection mirrors as described above. Theoretically, the material of these mirrors may be a semiconductor or a dielectric. Nevertheless, a dielectric multilayer film such as $SiO_2/HfO_2$, for example, is advantageous as described above in consideration of the material compatibility with the light-transparent chip 10.

The incorporation of the micro-resonator FPR into the light-transparent chip 10 can be attained by various methods. For example, in the case of constructing the chip 10 by bonding two glass plates 10a and 10b together as already described with reference to FIG. 10, a distributed Bragg reflection mirror is coated on one side of each of the glass sheets 10a and 10b by vacuum deposition, sputtering, or ion plating or the like. The deposition of $SiO_2$ film by plasma enhanced CVD on the Bragg reflection mirror of one glass plate is followed by channel formation using lithography, and subsequent bonding with the other glass plate. Alternatively, after the chip 10 is fabricated, the distributed Bragg reflection mirrors can be coated on both its outer surfaces.

Generally, since a channel is formed by isotropic wet etching, the cross section of the etched channel has a shape composed of a rectangle and one quarter of a circle attached to both sides of the rectangle. For the sake of avoiding loss of the confinement efficiency of the resonator, the excitation light Le preferably passes through only the rectangular part at the center of the separation channel 16. By using wet etching when the Bragg reflection mirror acts as an etch-stop layer or using dry etching, it is possible and ideal to form the channel with a rectangular cross section.

For the purpose of realizing the well-known stable resonance conditions in a Fabry-Perot resonator, the distributed Bragg reflection mirrors R1 and R2 may have a curvature. For the same reason, the excitation light Le does not need to be perfectly paralleled. In this sense, a concave lens 63 may not be always found necessary. The geometric structure may also admit various modifications. Optionally, the excitation light source 30 and the semiconductor light-detecting element 20 may be fabricated on the same substrate. This freedom of the geometric structure holds good in the embodiments illustrated in FIGS. 7 and 8, and is used in the following description.

It is known that the generation of an emission light by two-photon absorption can be more efficiently induced by using a pulse light having a high peak light intensity than by using a continuous wave light. This invention, therefore, proposes the embodiment illustrated in FIG. 7. Specifically, in this embodiment, a Q switch laser QSL is excited by being irradiated with the light (wavelength $\lambda 1$) from the surface-emitting laser diode 30 and it is consequently made to emit a short pulse laser light (wavelength $\lambda 2 > \lambda 1$) as the excitation light Le, which irradiates the sample plug in the separation channel 16.

The principle of the Q switch laser QSL itself is well known. This invention, in particular, is made to comprise a passive Q switch laser QSL comprised of a gain medium GM (for example Nd:YAG, Nd:YVO$_4$, and Yb:YAG or the like) and a saturable absorber SA (for example Cr;YAG or the like), on the end surfaces of which are formed a pair of mirrors (preferably distributed Bragg reflection mirrors) R3 and R4 having prescribed transmittance and reflectance, constituting a resonator with respect to the light of the aforementioned wavelength $\lambda 2$. On the other hand, it forms a configuration to insert a third mirror (preferably also a distributed Bragg reflection mirror) R5 between the gain medium GM and the saturable absorber SA, allowing light of wavelength $\lambda 2$ to be transmitted and light of wavelength $\lambda 1$ to be reflected. This enables the gain medium GM to be efficiently excited and, at the same time, efficiently prevents the light from the surface-emitting laser diode 30 from invading the separation channel 16. In fact, this configuration made it possible to greatly increase the instantaneous intensity of the laser beam as the excitation light Le and greatly elevate the fluorescence intensity due to two-photon absorption.

Further, the use of a semiconductor gain medium GM is advantageous in allowing easy control of the oscillation wavelength of the Q switch laser QSL. Further, a quantum well in the semiconductor gain medium results in a carrier confinement effect that enables an increase in the laser oscillation efficiency. In particular, in the case of this invention, the quantum well constituted of InGaAs on the GaAs substrate is suitable for exciting fluorophores useful for bioanalysis.

The use of a semiconductor for the saturable absorber SA (a structure known as SESAM (semiconductor saturable absorber mirrors) in which mirrors and a semiconductor saturable absorber SA are integrated together) brings the advantage of a wide absorption band and allows control of the absorption recovery time and optical intensity that saturates the absorption by adjusting the structure of the quantum well and the growth temperature. Further, when the In and Ga composition and the thickness of the InGaAs quantum well layer are fixed to produce a sufficient overlap between the gain spectrum of the gain medium GM and the absorption band of the saturable absorber SA, and the gain medium and saturable absorber are integrated on the same semiconductor substrate, there is no need for a mounting process, playing a large role in miniaturizing elements and enhancing the reliability, and further reducing the production cost.

Figure 7:
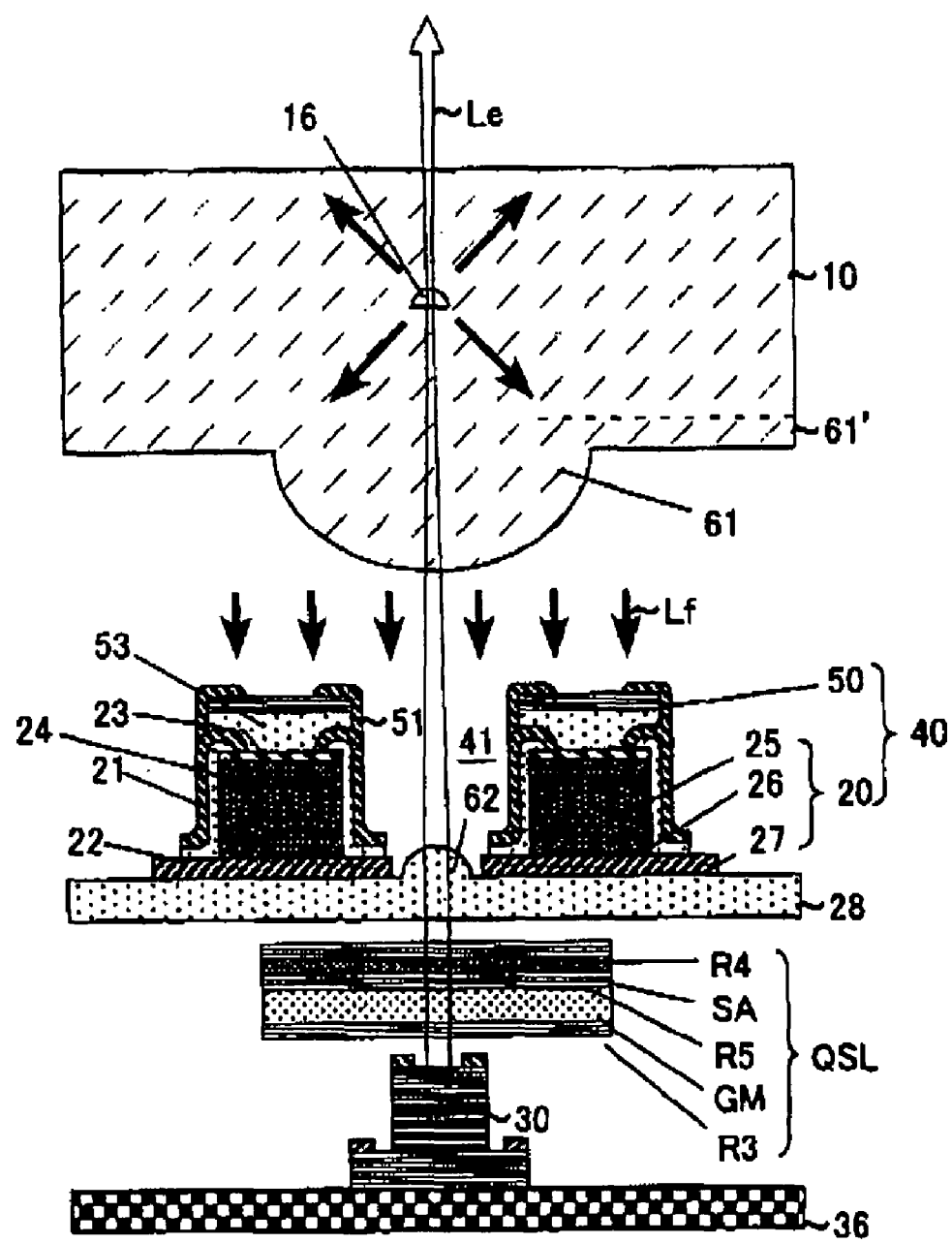
FIG. 7 is a schematic diagram of a fluorescence detecting device as a sixth embodiment of this invention.

What deserves attention is that it is a design in which all the individual important components in the embodiments illustrated in FIGS. 6 and 7 are disposed coaxially and consequently can be easily multiplexed in parallel. Of course, the surface-emitting laser 30 and the photodiode 20 may be monolithically integrated as already explained with respect to the embodiments of FIGS. 4 and 5 and, as a modified structure, the photodiode 20 and the optical filter 50 may be monolithically integrated on a light-transparent chip 10 as in the embodiment illustrated in FIG. 3.

Figure 8:
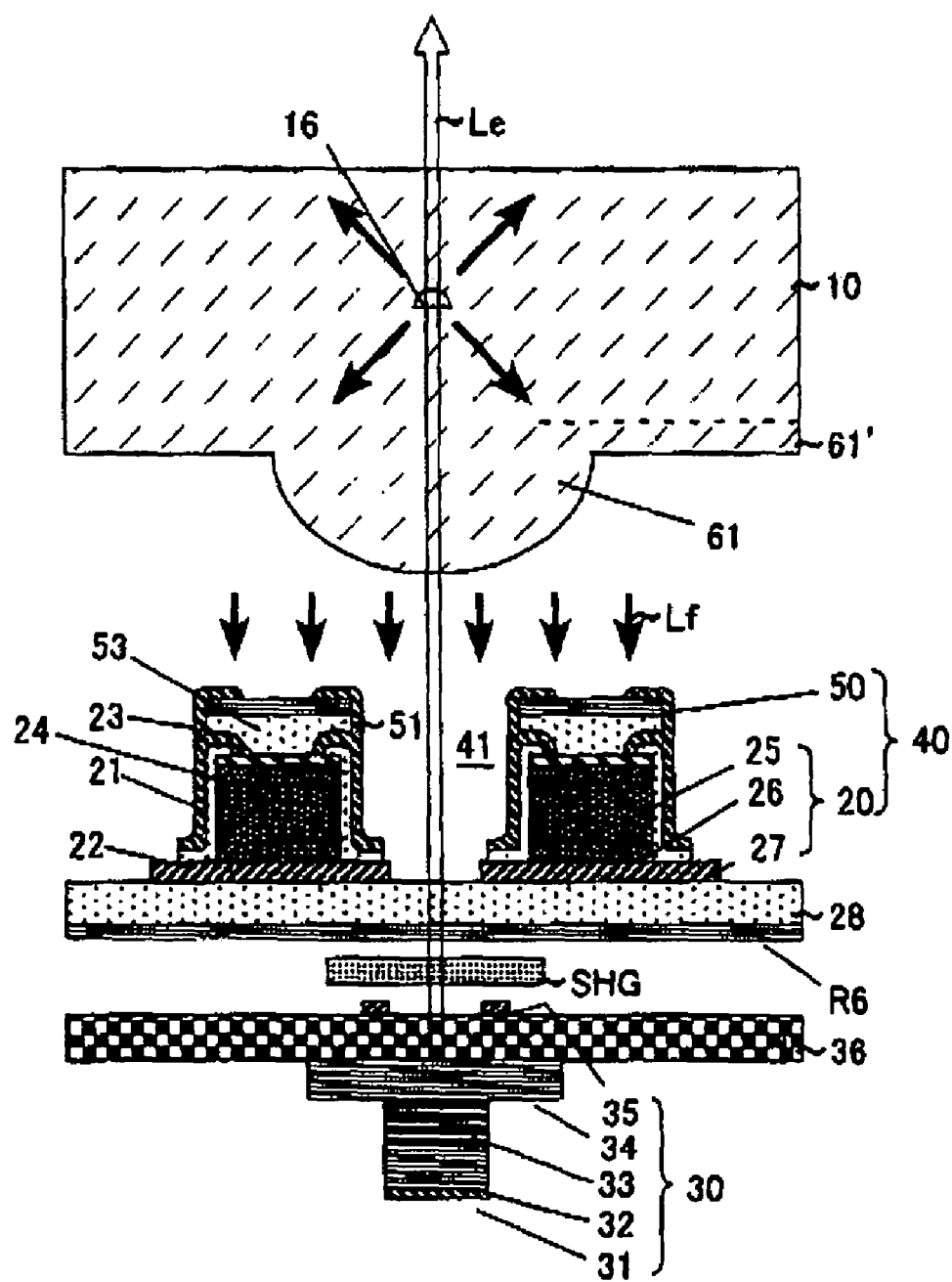
FIG. 8 is a schematic diagram of a fluorescence detecting device as a seventh embodiment of this invention.

Here, when the emphasis is on a design that enables a parallel implementation, as shown in FIG. 8, the device may be fabricated by inserting SHG elements such as KTP (=KTiOPO$_4$), KDP (=KH$_2$PO$_4$), or PPLN (=periodically poled LiNb$_3$) or the like into the resonator comprised of a Bragg reflection mirror R6 coated on the back surface of a glass substrate 18 and the distributed Bragg reflection mirror 34 of the surface-emitting laser 30, generating frequency-doubled light efficiently. In this case, fluorophores useful for bioanalysis can be excited even with ordinary one-photon absorption.

Figure 9:
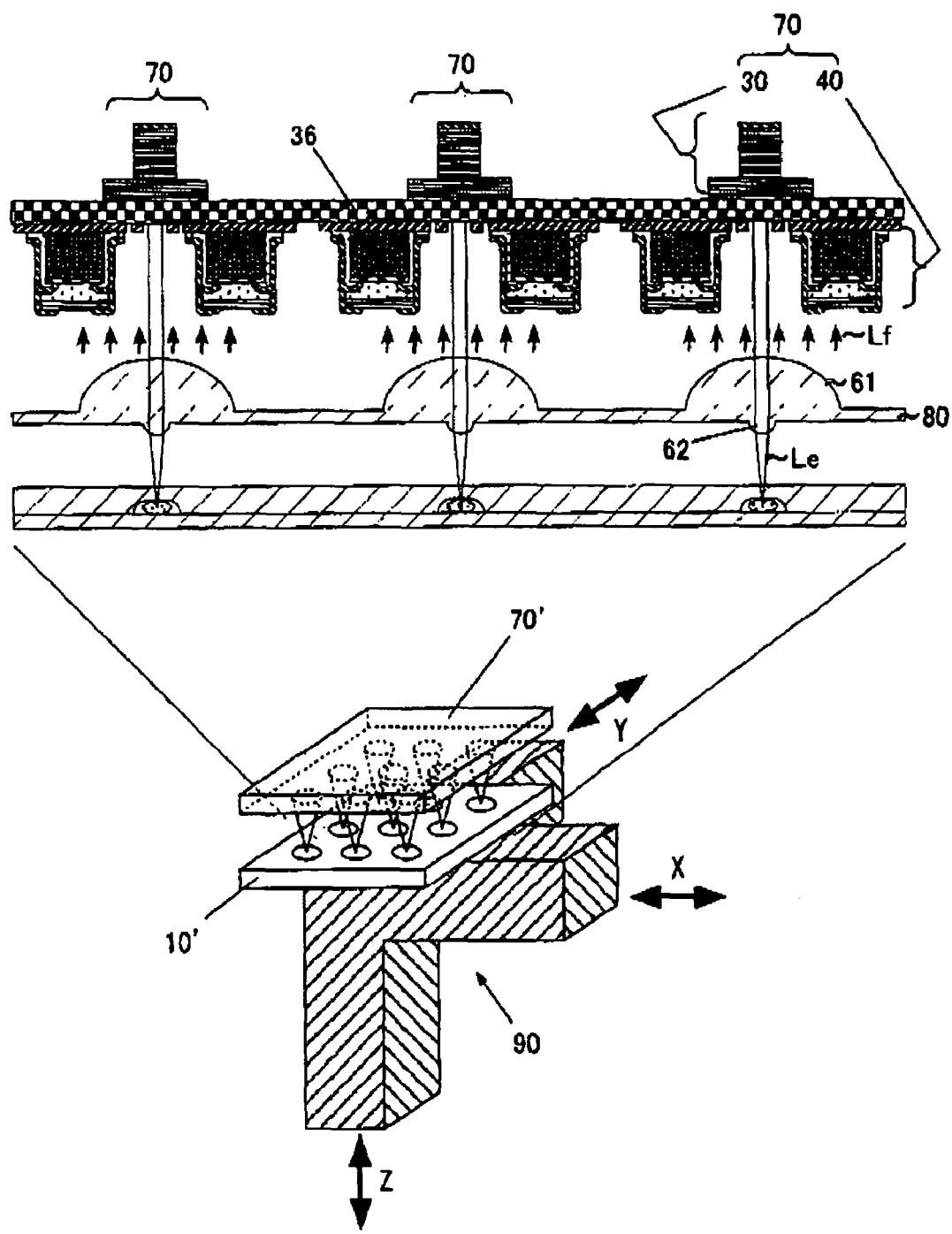
FIG. 9 is a schematic diagram of a fluorescence detecting device as a further example of an application of this invention.

The emission light detecting device according to this invention which has been explained with reference to FIG. 1 and FIGS. 4~8 can be developed as illustrated in FIG. 9 into a configuration in which an integrated structure based mainly on the surface-emitting laser diode 30 and the fluorescence detecting module 40 is regarded as one module 70 and arrays of such modules are arranged in one dimension or two-dimensions.

While the module 70 illustrated in the present illustration is different from that illustrated in FIG. 5 in respect of the converging microlens 62 not being fabricated on the substrate 36, it generally corresponds to that of FIG. 5, but may be substituted with the structures illustrated in FIG. 1 and FIGS. 4-8. The modules 70 are each furnished with a converging microlens 62 and a fluorescence collecting microlens 61, which are disposed as one lens module 80 partway along the light path of the excitation light and the fluorescence.

The one-dimensional array device can perform analysis of a plurality of electrophoretic channels in parallel and, when disposed along the length direction of the channels, can obtain an image of the inside channels at a certain time. The latter is particularly suited to isoelectric focusing (IEF) analysis. Isoelectric focusing is used in combination with gel electrophoresis (SDS-PAGE) reported in Document 4: Chen et al., "A Prototype Two-Dimensional Capillary Electrophoresis System Fabricated in Poly(dimethylsiloxane)," Anal. Chem. Vol. 74, No. 8 (Apr. 15, 2002), pp. 1772-1778, fulfilling a central role in the analysis of proteins.

Recently, the design of a microfluidic two-dimensional electrophoresis (IEF+SDS–PAGE) device has been reported. The use of two sets of one-dimensional arrays of modules 70 can easily cope with the design of this kind. The array of such modules in accordance with the present invention provides the major advantage that absolutely no restriction is imposed on the design of a microfluidic lab-on-a-chip, unlike a conventional scanning laser induced fluorescence detection system.

Further, according to this invention, as already described, the excitation due to the two-photon absorption can be limited to the vicinity of the focal point of the excitation light and, therefore, has an effective spatial filtering effect. When a two-dimensional array 70' of the modules 70 conforming to the configurations illustrated in FIG. 1 and FIGS. 4-7 is used as schematically depicted in the lower half of FIG. 9, therefore, it is possible to obtain a three-dimensional image of a given object in a chip 10' containing two-dimensionally arranged objects by scanning three-dimensionally with a scanning mechanism 90 using a piezoelectric element. For example, by patterning a self-assembled monolayer (SAM)

with soft lithography, cells are immobilized and disposed in an array on the glass chip 10', or cells are cultured in a microreactor array made of oxygen-permeable biocompatible PDMS (polydimethyl siloxane) and glass. In this case, using the cell array chip 10' makes it possible to obtain images of the cell array in parallel. This is useful for drug screening, for example, since it allows observation of numerous cells in parallel. It may of course be used for scanning in just a one-dimensional direction or in just a two-dimensional direction, or it could be used to scan only the individual modules 70 for some applications.

Modules conforming to the structure illustrated in FIG. 8 may be disposed in a two-dimensional array as illustrated in FIG. 9 without utilizing two-photon absorption. In this case, since there will not be the aforementioned spatial filtering effect, the resolution of a three-dimensional image of a given object will be poor compared with two-photon absorption. In some cases this will not pose a problem, and, depending on the data processing, it may be possible to improve the resolution. The resolution is improved more by inserting the converging microlens 62 partway along the light path of the excitation light as illustrated in FIG. 9, though not illustrated in FIG. 8. The reduction of the light irradiation area is effective in obtaining a better image in the case of one-photon absorption.

This invention has been described with reference to the preferred embodiments. It can be arbitrarily modified and freely applied to the extent that this does not depart from the gist of the invention.

Various examples of modification are conceivable. For example, the wavelength-multiplexed analysis can be realized by dividing the a-Si:H photodiode 20 into a plurality of parts and integrating optical filters possessing different spectral characteristics on each part. Analysis such as DNA sequencing can be realized by labeling adenine, guanine, thymine, and cytosine with fluorophores emitting fluorescence having different wavelengths.

In the imaging of cells illustrated in FIG. 9, a plurality of biological matters can be simultaneously traced by wavelength-multiplexed analysis. Being combined with the scanning mechanism, clearly further widens the range of applications. Similarly, in the detection of fluorescence as an emission light as described above, it is evident that this invention can be applied advantageously even when the fluorescence originates from a semiconductor quantum dot or a micro-object labeled therewith. This invention is clearly suitable for the detection of not only fluorescence but also phosphorescence.

Moreover, as the semiconductor light detecting element, a so-called photoconductor may be used in place of the photodiode described heretofore. The element using this photoconductor is very well known. The incorporation of this element in place of the semiconductor light detecting element which has been described heretofore, therefore, poses no difficulty to persons skilled in the art. Also, the preferred material for the photodiode is an a-Si:H as described above, but it is not limited thereto. Materials include such alloy materials as, for example, hydrogenated amorphous silicon-germanium alloys and hydrogenated amorphous silicon-carbide alloys which are easily fabricated by the same method by simply changing the source gas. These alloys have high sensitivity to longer wavelength light and shorter wavelength light compared to the a-Si:H, respectively. It is also possible to use microcrystalline silicon and alloy materials thereof which can be easily fabricated by the same method by merely changing the conditions of deposition such as the ratio of hydrogen dilution. When a surface-emitting laser diode is used as the excitation light source 30, not only a GaInAs/GaAs surface-emitting laser but also a GaAlAs/GaAs surface-emitting laser that emits light with a shorter wavelength and a GaInAsN/GaAs surface-emitting laser that emits light with a longer wavelength are also usable.

What is claimed is:

1. A micro-object emission light detecting device for detecting with a semiconductor light detecting element emission light emitted in the form of fluorescence or phosphorescence from a micro-object irradiated with excitation light emitted from an excitation light source; wherein said semiconductor light detecting element and said excitation light source are disposed coaxially or on one side, said micro-object emission light detecting device comprising:
   a Q switch laser that generates a short pulse laser in response to the irradiation with the excitation light, elevates a peak light intensity instantaneously, and irradiates the micro-object with a beam of short pulse laser as the excitation light; and
   a converging microlens that is inserted partway along a light path of the excitation light to converge the excitation light and elevate a peak light intensity of the excitation light and that irradiates the micro-object with the excitation light having the peak light intensity elevated;
   whereby emission light is generated from the micro-object due to two-photon absorption and detected with the semiconductor light detecting element
   wherein said Q switch laser is a passive type comprising a gain medium and a saturable absorber, and
   wherein the gain medium of said Q switch laser is a semiconductor with quantum well structure and the saturable absorber of said Q switch laser is also a semiconductor with quantum well structure.

2. A micro-object emission light detecting device according to claim 1, wherein the emission light emitted by said micro-object impinges on said semiconductor light detecting element via an optical filter possessing selective transmittance to said emission light.

3. A micro-object emission light detecting device according to claim 2, wherein the wavelength of said excitation light is a wavelength in the near infrared region.

4. A micro-object emission light detecting device according to claim 2, provided with a microlens for collecting emission light emitted from said micro-object, paralleling the collected light, and guiding the paralleled light to said optical filter.

5. A micro-object emission light detecting device according to claim 2, wherein at least the part of the side wall of said optical filter and said semiconductor light detecting element on which scattered light of said excitation light might fall incident is covered with a shielding layer.

6. A micro-object emission light detecting device according to claim 2, wherein an emission light detecting module comprised of said semiconductor light-detecting element and said optical filter, when viewed in a plan view, has a solid form of a circular or a polygonal shape with n vertices wherein n denotes an integer of not less than 3, said solid form has a part with a through hole of a circular or a polygonal shape with n vertices, and said excitation light passes through the interior of said through hole.

7. A micro-object emission light detecting device according to claim 2, wherein said semiconductor light detecting element is divided into a plurality of parts and the emission light emitted by said micro-object is passed through optical filters with different spectral characteristics and is impinged on each divided part of said semiconductor light detecting element.

8. A micro-object emission light detecting device according to claim 1, wherein said excitation light source is a surface emitting laser diode.

9. A micro-object emission light detecting device according to claim 1, wherein said semiconductor light-detecting element is a photodiode fabricated using a-Si:H material.

10. A micro-object emission light detecting device according to claim 1, wherein said semiconductor light-detecting element is a photoconductor fabricated using a-Si:H material.

11. A micro-object emission light detecting device according to claim 1, wherein said excitation light source and said semiconductor light-detecting element are integrated on the same substrate.

12. A micro-object emission light detecting device according to claim 1, characterized by said micro-object being a fluorophore or a semiconductor quantum dot or a microsample labeled with a fluorophore or a semiconductor quantum dot.

13. A micro-object emission light detecting device according to claim 1, wherein the wavelength of said excitation light is longer than the wavelength corresponding to a band gap of said semiconductor light detecting element and the wavelength of said emission light is shorter than the wavelength corresponding to a band gap of said semiconductor light detecting element.

14. A micro-object emission light detecting device according to claim 1, wherein the gain medium of said Q switch laser and the saturable absorber are monolithically integrated on the same semiconductor substrate.

15. A micro-object emission light detecting device for detecting with a semiconductor light detecting element emission light emitted in the form of fluorescence or phosphorescence from a micro-object irradiated with excitation light emitted from an excitation light source; wherein said semiconductor light detecting element and said excitation light source are disposed coaxially or on one side, said micro-object emission light detecting device comprising:

a Q switch laser that generates a short pulse laser in response to the irradiation with the excitation light, elevates a peak light intensity instantaneously, and irradiates the micro-object with a beam of short pulse laser as the excitation light; and a converging microlens that is inserted partway along a light path of the excitation light to converge the excitation light and elevate a peak light intensity of the excitation light and that irradiates the micro-object with the excitation light having the peak light intensity elevated;

whereby emission light is generated from the micro-object due to two-photon absorption and detected with the semiconductor light detecting element, wherein said Q switch laser is a passive type comprising a gain medium and a saturable absorber wherein the gain medium of said Q switch laser and the saturable absorber are quantum wells formed of InGaAs grown on a GaAs substrate, and the composition of the In and the Ga and the thickness of the InGaAs quantum well layer is so fixed as to give rise to an overlap between the gain curve of said gain medium and the absorption band of said saturable absorber.

* * * * *